United States Patent [19]

Pastor et al.

[11] Patent Number: 5,654,434
[45] Date of Patent: *Aug. 5, 1997

[54] HYDROGEN PEROXIDE OXIDATION OF 4-HYDROXY-2, 2, 6, 6-TETRAMETHYLPIPERIDINE

[75] Inventors: Stephen D. Pastor, Danbury, Conn.; Andrea R. Smith, Wingdale, N.Y.; Kurt M. Bessonen, Mobile, Ala.

[73] Assignee: Ciba-Geigy Corporation, Tarrytown, N.Y.

[ * ] Notice: The term of this patent shall not extend beyond the expiration date of Pat. No. 5,269,426.

[21] Appl. No.: 555,822

[22] Filed: Nov. 9, 1995

[51] Int. Cl.$^6$ .................................................. C07D 211/94
[52] U.S. Cl. ........................................................ 546/242
[58] Field of Search ...................................... 546/219, 242

[56] References Cited

U.S. PATENT DOCUMENTS

| | | | |
|---|---|---|---|
| 4,665,185 | 5/1987 | Winter et al. | 546/184 |
| 5,254,760 | 10/1993 | Winter et al. | 585/5 |
| 5,416,215 | 5/1995 | Büschken et al. | 546/184 |

OTHER PUBLICATIONS

J. Keana, Chemical Reviews, vol. 78 No. 1 (1978) pp. 38–64.

M. Dagonneau et al., Synthesis, Nov. 1984 pp. 895–916.

E. Rozantsev et al., Synthesis, Aug. 1971, pp. 401–414.

E. Rozantsev et al. Synthesis, Apr. 1971, pp. 190–202.

G. Sosnovsky et al., Z. Naturfer–Ch. 31b, pp. 1376–1378 (1976).

S. Zakrzewski, Journal of. Prakt. Chemie Band, 327, Heft 6, 1985 S. 1011–1014.

M. E. Brik, Tetrahedron Letters, vol. 36 No. 31 pp. 5519–5522 (1995).

E. Rauckman et al. Synthetic Comm. 5(6) 409–413 (1975).

Levina, T.M. et al, Dokl. Akad. Nauk. SSSR 1981, 261(1), pp. 109–110, see english abstract.

Hudson, A. et al, J. Chem. Soc. B, 1968, 268, pp. 251–253.

*Primary Examiner*—C. Warren Ivy
*Assistant Examiner*—Garth M. Dahlen
*Attorney, Agent, or Firm*—Luther A. R. Hall

[57] ABSTRACT

An environmentally friendly process is described for the preparation of 4-hydroxy-2,2,6,6-tetramethylpiperidine-N-oxyl by the direct hydrogen peroxide oxidation of 4-hydroxy-2,2,6,6-tetramethylpiperidine in the absence of any catalyst.

7 Claims, No Drawings

HYDROGEN PEROXIDE OXIDATION OF 4-HYDROXY-2, 2, 6, 6-TETRAMETHYLPIPERIDINE

The instant invention pertains to the hydrogen peroxide oxidation of 4-hydroxy-2,2,6,6-tetramethylpiperidine to the corresponding 4-hydroxy-2,2,6,6-tetramethylpiperidine-N-oxyl compound using hydrogen peroxide without any catalyst.

BACKGROUND OF THE INVENTION 2,2,6,6-Tetramethylpiperidine and its derivatives are important spin traps for labelling biological molecules. This is illustrated in a number of reviews as follows: J. F. W. Keana, Chemical Reviews, 78, 37 (1978); M. Dagonneau et al., Synthesis, 1984, 895; E. G. Rozantsev et al., Synthesis 1971, 401; and E. G. Rozantsev et al., Synthesis, 1971, 190.

Such compounds are also disclosed as inhibitors for preventing the premature polymerization of vinyl monomers as seen in U.S. Pat. No. 5,254,760.

The oxidation of 4-substituted 2,2,6,6-tetramethylpiperidines to the corresponding N-oxyl derivatives is known to occur by a number of different processes. U.S. Pat. No. 4,665,185 describes using tert-butyl hydroperoxide with transition metal (molybdenum) catalysts. G. Sosnovsky et al., Z. Naturforsch. 31b, 1376 (1976); J. Zakrzewski, J. Prakt. Chem., 327, 1011 (1985) and E. G. Rozantsev et al., Synthesis, 1971, 190 each teach the use of hydrogen peroxide with sodium tungstate catalyst. U.S. Pat. No. 5,416,215 teaches the use of hydrogen and selected divalent metal salts. M. E. Brik, Tetrahedron Letters, 36, 5519 (1995) teaches the oxidation of secondary amines to nitroxides using Oxone® (potassium peroxomonosulfate) in aqueous buffered solutions.

E. J. Rauckman et al., Syn. Communications 5(6), 409 (1975) describe inter alia the oxidation of secondary amines to nitroxides using catalytic amounts of sodium tungstate in the presence of acetonitrile, methanol, hydrogen peroxide and sodium bicarbonate at room temperature for two days to give the oxyl compound in a yield of 85%. The required presence of the known sodium tungstate catalyst clearly differentiates the Rauckman process from the instant process where no catalyst is present.

J. Zakrzewski, J. prakt. Chem., 327(6), 1011 (1985) does teach that 30% hydrogen peroxide in the presence of a three molar excess of sodium carbonate gives the oxyl compound in a yield of 73% after two days. The instant process requires no catalyst and gives the oxyl compound in very high conversion in less than five hours. The instant process is clearly different from the process of Zakrzewski.

In a copending application Ser. No. 08/555,823, a process is described involving the use of an environmentally safe and friendly catalyst which avoids the presence of transition metals in waste waters. While sodium bicarbonate and sodium carbonate are easily handled, are economically inexpensive and cause no adverse environmental conditions, the instant process also gives the desired N-oxyl compounds in high yields and conversions without the use for costly and environmetally hazardous transition metals or divalent metal ions.

The instant process involves a still simpler method to prepare the desired N-oxyl compound by using hydrogen peroxide in the absence of any catalyst at a moderate temperature. There is no undesirable waste by-product of the instant process.

DETAILED DISCLOSURE

The instant invention pertains to an environmentally friendly process for the preparation of 4-hydroxy-2,2,6,6-tetramethylpiperidine-N-oxyl which comprises oxidizing 4-hydroxy-2,2,6,6-tetramethylpiperidine with an aqueous hydrogen peroxide solution in the absence of any catalyst at a temperature of 80°–99° C.; with the oxidation reaction being complete in less than 5 hours.

The instant process may be completed in as little as two hours. The instant process is clearly differentiated from that of Zakrzewski which requires two days at ambient temperature to achieve a 73% yield of product using a three molar excess of sodium carbonate catalyst.

Preferably the aqueous hydrogen peroxide is 30–50% by weight hydrogen peroxide; most preferably 50% by weight hydrogen peroxide.

Preferably the temperature range for the process is 90°–99° C.

A preferred embodiment of the process involves adding the hydrogen peroxide continuously over a 2–4 hour period to the reaction mixture.

The instant process may optionally have a metal passivator or chelator present. The EDTA type chelators such as ethylenediaminetetraacetic acid disodium salt are particularly suited since they remove trace amounts of iron or other metals encountered during manufacturing processes without interfering with the reaction. Iron or other metals may decompose the hydrogen peroxide unless removed by such a chelator.

The course of the reaction is monitored by GLC to determine the conversion of the N—H to N-oxyl compound. In theory 1.5 equivalents of hydrogen peroxide are needed to oxidize one equivalent of the starting material to the corresponding N-oxyl compound. In the instant process, the mount of aqueous hydrogen peroxide used is from 1.5 to 4 equivalents per equivalent of 4-hydroxy-2,2,6,6-tetramethylpiperidine.

Any excess hydrogen peroxide may be destroyed using catalytic quantities of platinum or palladium on charcoal.

Alternatively, any excess hydrogen peroxide may be destroyed facilely by the addition of sodium sulfite at an elevated pH (using sodium hydroxide) followed by the addition of acid for neutralization.

The N-oxyl compound may be isolated by using rotary evaporation of the water solvent under vacuum or other conventional means.

Early workers showed that the oxidation of the starting material to the corresponding N-oxyl using hydrogen peroxide can proceed without a catalyst, but that very long times are needed to achieve any meaningful amount of product. The advantages of the instant process, besides the clear environmental benefits, are better conversion with time and a quicker initiation of the oxidation reaction. The initiation of the reaction without catalyst can be variable, leading to different levels of hydrogen peroxide built up in the reaction mixture, but the strong exotherm at the initiation of the reaction can be anticipated and controlled when the reaction is run without catalyst at an elevated temperature as in the instant process.

The following examples are for illustrative purposes only and are not to be construed to limit the scope of the instant invention in any manner whatsoever.

EXAMPLE 1

4-Hydroxy-2,2,6,6-tetramethylpiperidine-N-oxyl

To a solution of 100 g (0.636 mol) of 4-hydroxy-2,2,6,6-tetramethylpiperidine in 80 g of deionized water at 80° C. is added over a four-hour period using a syringe pump 86.4 g (1.27 mol) of 50% hydrogen peroxide. The reaction mixture is stirred for 3 additional hours. The conversion to 4-hydroxy-2,2,6,6-tetramethylpiperidine-N-oxyl is 99.4% as determined by GLC analysis.

EXAMPLE 2

4-Hydroxy-2,2,6,6-tetramethylpiperidine-N-oxyl

A solution of 126.78 g (0.81 mol) of 4-hydroxy-2,2,6,6-tetramethylpiperidine and 0.74 g (0.002 mol) of ethylenediaminetetraacetic acid disodium salt dihydrate in 100 mL of distilled water is heated to 70° C. To the resultant mixture is added over a two-hour period using a syringe pump 160 mL (2.61 mol) of 50% hydrogen peroxide. The temperature of the reaction mixture is increased to 95°–99° C. over the first 20 minutes of the addition of the hydrogen peroxide and then the reaction mixture is maintained at that temperature till all the hydrogen peroxide is added. Upon completion of the slow addition of hydrogen peroxide, the conversion to 4-hydroxy-2,2,6,6-tetramethylpiperidine-N-oxyl is 99.1% as determined by GLC analysis.

It is clear that the instant process gives the desired N-oxyl compound in excellent conversion in the absence of any catalyst using hydrogen peroxide. This process affords the desired N-oxyl end product without the concomitant undesired heavy metal catalyst waste products which are environmentally hazardous. The by-products of the instant process such as water do not present any severe pollution problems in waste water streams.

What is claimed is:

1. An environmentally friendly process for the preparation of 4-hydroxy-2,2,6,6-tetramethylpiperidine-N-oxyl which comprises oxidizing 4-hydroxy-2,2,6,6-tetramethylpiperidine with an aqueous hydrogen peroxide solution in the absence of any catalyst at a temperature range of 80°–99° C. and in the presence of a metal passivator.

2. A process according to claim 1 wherein the temperature range for the process is 90°–99° C.

3. A process according to claim 1 wherein the aqueous hydrogen peroxide is 30–50% by weight hydrogen peroxide.

4. A process according to claim 3 wherein the aqueous hydrogen peroxide is 50% by weight hydrogen peroxide.

5. A process according to claim 1 wherein the hydrogen peroxide is added continuously over a 2 to 4 hour-period to the reaction mixture.

6. A process according to claim 1 wherein the metal passivator is ethylenediaminetetraacetic acid disodium salt.

7. A process according to claim 1 wherein the amount of aqueous hydrogen peroxide is from 1.5 to 4 equivalents per equivalent of 4-hydroxy-2,2,6,6-tetramethylpiperidine.

* * * * *

UNITED STATES PATENT AND TRADEMARK OFFICE
CERTIFICATE OF CORRECTION

PATENT NO. : 5,654,434

DATED : August 5, 1997

INVENTOR(S) : Stephen D. Pastor, et al.

It is certified that error appears in the above-identified patent and that said Letters Patent is hereby corrected as shown below:

On cover page please amend section [*] to read as follows:

-- [*] Notice: The term of this patent shallnot extend beyond the expiration date of Pat. No. 5,629,426 --.

Signed and Sealed this

Twenty-third Day of December, 1997

Attest:

BRUCE LEHMAN

Attesting Officer

Commissioner of Patents and Trademarks